United States Patent
Zardini

(10) Patent No.: US 9,931,676 B2
(45) Date of Patent: Apr. 3, 2018

(54) TUNNEL-TYPE MACHINE FOR WASHING OBJECTS

(71) Applicant: STEELCO SPA, Riese Pio X (IT)

(72) Inventor: Fabio Zardini, Castelfranco Veneto (IT)

(73) Assignee: STEELCO SPA, Riese Pio X (IT)

(*) Notice: Subject to any disclaimer, the term of this patent is extended or adjusted under 35 U.S.C. 154(b) by 209 days.

(21) Appl. No.: 14/890,890

(22) PCT Filed: May 13, 2014

(86) PCT No.: PCT/IB2014/061391
§ 371 (c)(1),
(2) Date: Nov. 12, 2015

(87) PCT Pub. No.: WO2014/184731
PCT Pub. Date: Nov. 20, 2014

(65) Prior Publication Data
US 2016/0089699 A1     Mar. 31, 2016

(30) Foreign Application Priority Data
May 13, 2013  (IT) .............................. UD2013A0064

(51) Int. Cl.
*B08B 3/02* (2006.01)
*B08B 13/00* (2006.01)

(52) U.S. Cl.
CPC ............... *B08B 3/02* (2013.01); *B08B 13/00* (2013.01); *A61L 2202/17* (2013.01); *A61L 2202/23* (2013.01)

(58) Field of Classification Search
None
See application file for complete search history.

(56) References Cited

U.S. PATENT DOCUMENTS 4,169,408 A    10/1979  Mencacci
5,783,156 A *   7/1998  Renzi .................. F26B 5/06
                                                      312/1

(Continued)

FOREIGN PATENT DOCUMENTS

DE    3321 195 A1    12/1984
EP    0 312 022 A2    4/1989

(Continued)

OTHER PUBLICATIONS

Search Report and Written Opinion for PCT/IB2014/061391, dated Aug. 18, 2014.

*Primary Examiner* — Jason Ko
(74) *Attorney, Agent, or Firm* — Marshall, Gerstein & Borun LLP

(57) ABSTRACT

A tunnel-type machine to wash objects comprises a containing structure which internally delimits a work volume and is provided with at least an entrance door to feed the objects in a loading direction. The work volume comprises at least two processing chambers contiguous in the loading direction, a single separation door is provided between the two processing chambers, and is mobile through a passage aperture of the containing structure. At least a front packing is provided between the two processing chambers, and at least an upper packing is provided at the passage aperture, and the separation door is configured to contact, in a closed and separated position of the two chambers, both the front packing and the upper packing.

17 Claims, 3 Drawing Sheets

(56) References Cited

U.S. PATENT DOCUMENTS

| | | | |
|---|---|---|---|
| 6,297,479 | B1 | 10/2001 | Wefers |
| 2008/0127560 | A1* | 6/2008 | Harvey ................ E05F 15/686 49/199 |

FOREIGN PATENT DOCUMENTS

| | | |
|---|---|---|
| EP | 0 992 246 A2 | 4/2000 |
| WO | WO-02/051450 A1 | 7/2002 |
| WO | WO-03/047637 A1 | 6/2003 |
| WO | WO-2006/073909 A2 | 7/2006 |
| WO | WO-2009/092518 A1 | 7/2009 |

* cited by examiner

TUNNEL-TYPE MACHINE FOR WASHING OBJECTS

FIELD OF THE INVENTION

The present invention concerns a machine for washing objects, in particular a so-called tunnel-type washing machine, in which successive washing cycles are carried out in processing chambers disposed one after the other.

Here and hereafter, and also in the claims, by the term "washing" we mean, in their entirety, both operations for the pre-treatment of objects, such as pre-washing with hot or cold water and/or detergents or other chemical products, and washing operations proper, and also drying operations. Heat disinfection, sterilization and decontamination using particularly aggressive and dangerous decontamination substances, such as oxygenated water, are also comprised in the term "washing".

By way of example, the objects that can be washed in the washing machine in question can be laboratory instruments, used for analysis or research, instruments used in the pharmaceutical sector, or instruments from the medical sector, surgical instruments or similar or comparable instruments, without however excluding the application of the present invention to the washing of objects in general.

BACKGROUND OF THE INVENTION

It is known to make machines for washing objects, generally contained in containers, such as object-holding racks, which are fed inside a suitable washing chamber by means of feed means, for example a belt, where the washing cycle is carried out.

Normally, at least one door is provided, associated with an entrance aperture which is mobile vertically and is driven by an opening and closing mechanism to assume a high or open position in which it allows the objects to be washed to enter into the washing chamber, and a low or closed position in which, in cooperation with fluidic sealing means, it seals the washing chamber from the outside. In pass-through washing machines, a door is also provided associated with an exit aperture, in the position opposite the entrance aperture.

Tunnel-type washing machines are also known, which are provided with a plurality of distinct processing chambers, disposed in succession to each other and inside which one or more steps of the desired washing procedures are carried out.

These known washing machines are defined by the juxtaposition of two or more independent processing chambers that consist of physically autonomous units put adjacent to each other, or two or more washing machines with a single chamber located in succession.

Each processing chamber of known tunnel-type machines is configured to be fluidically sealed during use, both with regard to the outside environment and also with regard to the contiguous processing chamber or chambers.

Furthermore, the processing chambers of known tunnel-type machines are each provided with an entrance door and a possible exit door that put contiguous chambers in communication with each other and allow to transfer the objects from one chamber to the other in order to carry out successive washing operations.

Consequently, in known tunnel-type machines there are generally two doors present in the intermediate communication zones between two contiguous processing chambers, in particular an exit door of one processing chamber and an entrance door of the successive processing chamber.

Control and command devices can be connected to the opening and closing mechanisms of the doors of the processing chambers, which are configured to manage the opening and closing of the doors, for example in terms of timing or possible synchronization of said operations.

The doors are configured to obtain the fluidic seal mentioned above, normally in association with fluidic seal means disposed peripherally around the doors and/or the apertures that they have to seal. In particular, to obtain said fluidic seal, known washing machines are provided with devices, either active or passive, associated with the fluidic seal means and/or the doors, that determine a reciprocal thrust of the doors and the fluidic seal means. The thrust is generally used to deform the fluidic seal means and consequently to obtain the perfect seal of the apertures by the corresponding doors.

One disadvantage of known washing machines is that in order to seal the processing chambers, both reciprocally and from the outside, they require a large number of components, i.e. doors, opening and closing mechanisms, thrust devices, control and command devices, fluidic seal means, possible devices to control the seal. This large number of components leads to constructional and management complexity of said known washing machines, and also to high production and maintenance costs, which affect the costs of the washing process.

Document U.S. Pat. No. 6,297,479 describes a drying or heat processing apparatus provided with a central processing chamber, a loading chamber upstream and an unloading chamber downstream, the latter two being provided with closing doors at entrance and exit with sealing elements.

Document EP-A-0.992.246 describes a sterilization tunnel for pharmaceutical containers provided with an entrance zone, a sterilization zone, a cooling zone, a transport belt and intermediate walls to separate the various zones.

Document WO-A-03/047637 describes a sterilization tunnel for pharmaceutical containers provided with an entrance zone, a sterilization zone, two cooling zones, a transport belt and closing elements between the various zones.

Document WO-A-02/051450 describes a system for the continuous sterilization of bottles formed by contiguous modules, including an entrance module with a laminar flow of air, a sterilization module with a laminar flow of hot air and a cooling module with a laminar flow of cooling air.

Document U.S. Pat. No. 4,169,408 describes a cooking and cooling system provided with an entrance section, a cooking chamber and an exit and cooling section. Between the entrance section and the cooking chamber a vertically mobile door is provided that can be closed in a sealed manner.

Document EP-A-0.312.022 describes a device for sterilizing glass bottles provided with laminar flow units.

Document DE-A-3321195 describes a device for sterilizing glass containers.

Document WO-A-2009/092518 describes a device for drying objects, in particular the painted bodies of vehicles, provided with a drying tunnel.

Document WO-A-2006/073909 describes a tunnel for sterilizing foodstuffs in pre-packed containers.

Purpose of the present invention is to obtain a washing machine, such as a tunnel-type washing machine provided with a plurality of processing chambers in series, which allows to wash objects effectively, guaranteeing the fluidic seal of the respective processing chambers both reciprocally and with respect to the outside, and which at the same time allows to reduce overall costs, understood in terms of production, transport and bulk, as well as in terms of maintenance and washing.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purpose, a tunnel-type machine for washing objects according to the present invention comprises a containing structure which internally delimits a single work volume and is provided with at least an entrance door to feed the objects to be washed in a loading direction.

According to one aspect of the present invention, the work volume comprises at least two processing chambers contiguous in the loading direction and a single separation door is provided between the two processing chambers. Moreover, the separation door is mobile through a passage aperture of the containing structure and first fluidic seal means, in particular at least one front packing, are provided between the two processing chambers, while second fluidic seal means, in particular at least one upper packing, are provided at the passage aperture. In particular, the separation door is configured to contact both the first fluidic seal means, in particular the at least one front packing, and also the second fluidic seal means, in particular the at least one upper packing.

In this way we achieve the advantage of determining, with a single separation door, the fluidic separation and the reciprocal seal with respect to the outside of two contiguous processing chambers in their separation zone, for example in an intermediate zone of the containing structure.

This translates into a conspicuous and advantageous reduction of the components of the tunnel-type washing machine, which consequently allows to reduce the production costs and facilitates the assembly procedures of the machine.

In the same way, the present invention also allows to reduce the costs of the washing process, allowing to reduce the maintenance and management times of the tunnel-type washing machine.

According to some aspects of the present invention, the separation door is mobile along a movement plane between an open position, in which it is located at least largely outside the work volume, and a closed position, inside the work volume. Moreover the passage aperture, provided in the containing structure to allow the passage of the separation door, lies on a lying plane transverse to the movement plane of the separation door.

In some forms of embodiment, the first fluidic seal means, in particular the at least one front packing, positioned inside said containing structure, lie on a sealing plane parallel to the movement plane and are positioned along at least the greater part of the perimeter of the cross section of the containing structure.

Other forms of embodiment provide that the second fluidic seal means, in particular the at least one upper packing, are disposed around the whole perimeter edge that delimits the passage aperture and lie on a plane parallel to the lying plane of the passage aperture itself.

In the closed position, the separation door is configured to cooperate with the second fluidic seal means, in particular the at least one upper packing, in order to fluidically separate the first processing chamber and the second processing chamber from the outside of the work volume.

In some forms of embodiment, the tunnel-type washing machine according to the present invention comprises movement means configured to move the separation door from the closed position, in which it lies on the movement plane, toward the sealing plane, in order to make it assume a further sealing position, in which the movement means keep the separation door thrust against the first fluidic seal means, in particular the at least one front packing, deforming them under compression to fluidically separate the first processing chamber and the second processing chamber.

Further aspects of the present invention provide that the movement means comprise a plurality of thrust units, associated symmetrically to peripheral lateral parts of the separation door and to the containing structure. Each thrust unit is defined by the coupling of a protruding element, such as a pin or an overhang, or a cam or a guide wheel, and a peripheral guide wall inclined with respect to the movement plane and to the sealing plane. In particular, the protruding element and the peripheral guide wall are configured to reciprocally slide one on the other or vice versa, in order to thrust the separation door toward the sealing plane.

The various aspects and characteristics described in the present description can be applied individually where possible. These individual aspects, for example aspects and characteristics described in the attached dependent claims, can be the object of divisional applications.

It is understood that any aspect or characteristic that is discovered, during the patenting process, to be already known, shall not be claimed and shall be the object of a disclaimer.

BRIEF DESCRIPTION OF THE DRAWINGS

These and other characteristics of the present invention will become apparent from the following description of some forms of embodiment, given as a non-restrictive example with reference to the attached drawings wherein.

Figure 1:
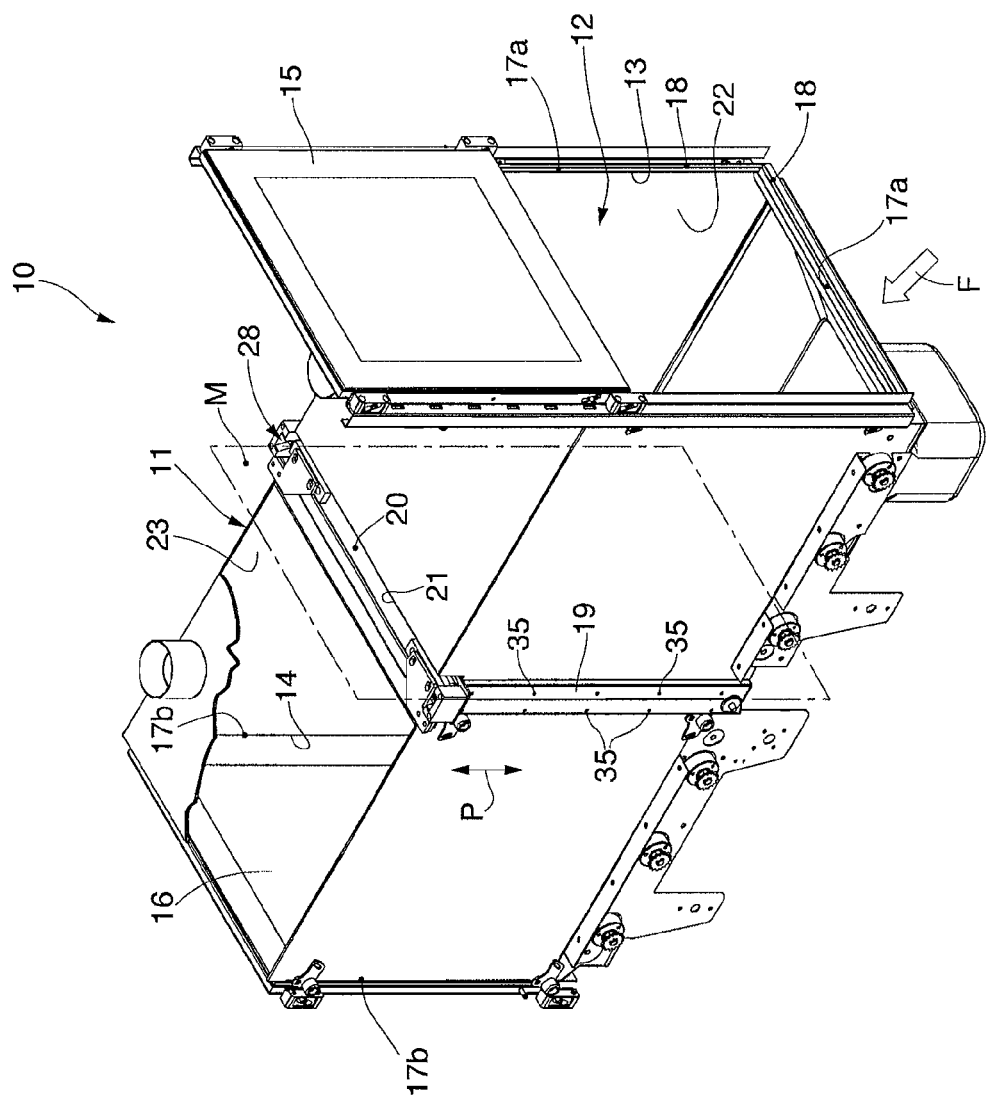
FIG. 1 is a three-dimensional view of a tunnel-type washing machine according to the present invention.

To facilitate comprehension, the same reference numbers have been used, where possible, to identify identical common elements in the drawings. It is understood that elements and characteristics of one form of embodiment can conveniently be incorporated into other forms of embodiment without further clarifications.

DETAILED DESCRIPTION OF SOME FORMS OF EMBODIMENT

We shall now refer in detail to the various forms of embodiment of the present invention, of which one or more examples are shown in the attached drawing. Each example is supplied by way of illustration of the invention and shall not be understood as a limitation thereof. For example, the characteristics shown or described insomuch as they are part of one form of embodiment can be adopted on, or in association with, other forms of embodiment to produce another form of embodiment. It is understood that the present invention shall include all such modifications and variants.

With reference to the attached drawings, the reference number 10 denotes in its entirety a tunnel-type washing machine according to the present invention, which can be used, for example but not restrictively, to perform pre-washing operations, with hot or cold water and/or with detergents or other chemical products, or to perform washing operations proper, or also drying, heat disinfecting, sterilization or decontamination of objects, such as for example surgical instruments, or laboratory instruments or similar or comparable instruments.

The tunnel-type washing machine 10 comprises a containing structure 11 with a box-like shape, hollow inside and delimiting a single work volume 12 inside which, in a determinate working direction, the different operations or steps of a washing cycle occur in sequence, to wash the objects in question.

With reference to FIG. 1, the containing structure 11 has an entrance aperture 13, in this case made at the front, used to load or insert, manually or automatically, the objects to be washed in the work volume 12. The objects to be washed can be loose or organized and disposed in racks or similar containers.

Generally, loading occurs in a loading direction (indicated in FIG. 1 by the arrow F). The loading direction F is transverse, for example orthogonal, to the plane on which the entrance aperture 13 lies. The loading direction F generally coincides with the working direction through the work volume 12 as above.

The tunnel-type washing machine 10 can be for example the pass-through type. In the example shown in FIG. 1, the tunnel-type washing machine 10 includes for example not only the entrance aperture 13 but also a rear aperture 14, from which the washed objects exit from the work volume 12 at the end of the process or processes to which they have been subjected inside it.

There is nothing to prevent the present invention being applied to tunnel-type washing machines with apertures made differently, such as at the side or top, and also tunnel-type washing machines with a single entrance and exit aperture.

In the attached drawings, merely by way of example and for convenience of illustration, the shape of the containing structure 11 is substantially parallelepiped, while other polyhedral or spherical or ovoid or irregular shapes are not excluded.

In the same way, the shape of the entrance aperture 13 and exit aperture 14 is shown as rectangular in the drawings, although other polygonal or circular or elliptic or irregular shapes are not excluded.

An entrance door 15 and in this case an exit door 16 are provided, to respectively close the entrance aperture 13 and the exit aperture 14 during the washing steps.

The entrance aperture 13 and exit aperture 14 are provided respectively with perimeter edges 17a and perimeter edges 17b with which packings 18 cooperate. During washing, the packings 18 are thrust or compressed by the respective entrance door 15 and exit door 16 to obtain a watertight closure of the work volume 12.

In particular, in FIG. 1 the entrance door 15 is shown in an open position, that is, almost completely outside the entrance aperture 13, while the exit door 16 is shown in a closed position, that is, to completely cover the exit aperture 14.

In a longitudinal intermediate zone, that is, in the loading direction F of the containing structure 11, the tunnel-type washing machine 10 has a mobile separation door 20, configured to selectively separate the work volume 12 and define, in a closed position, inside the containing structure 11, two processing chambers 22, 23 in succession, in which respective processing operations of the washing cycle are performed.

With reference to FIG. 1, moreover, in said longitudinal intermediate zone, the tunnel-type washing machine 10 can include for example two movement guides 19, linear, made laterally with respect to the cross section of the containing structure 11.

The movement guides 19 are configured to guide the translation of the separation door 20 in a direction of movement P, for example vertical, such as transverse or substantially orthogonal with respect to the loading direction F.

The movement guides 19 can be made in a piece in the containing structure 11, or can be applied to it, for example by means of attachment members, such as attachment screws 35.

In the attached drawings, the movement guides 19 have the shape of an L-shaped angular section bar, but other shapes, for example C-shaped, can be used for the same purpose.

In correspondence with the intermediate zone, where the separation door 20 is provided and where for example the movement guides 19 are provided, the containing structure 11 includes a passage aperture 21 through which the separation door 20 passes during its motion of translation from outside to inside the containing structure 11 and vice versa.

During said motion of translation the separation door 20, guided for example by the movement guides 19, lies on a movement plane M substantially parallel to the plane on which the entrance aperture 13 and exit aperture 14 lie.

Figure 2:
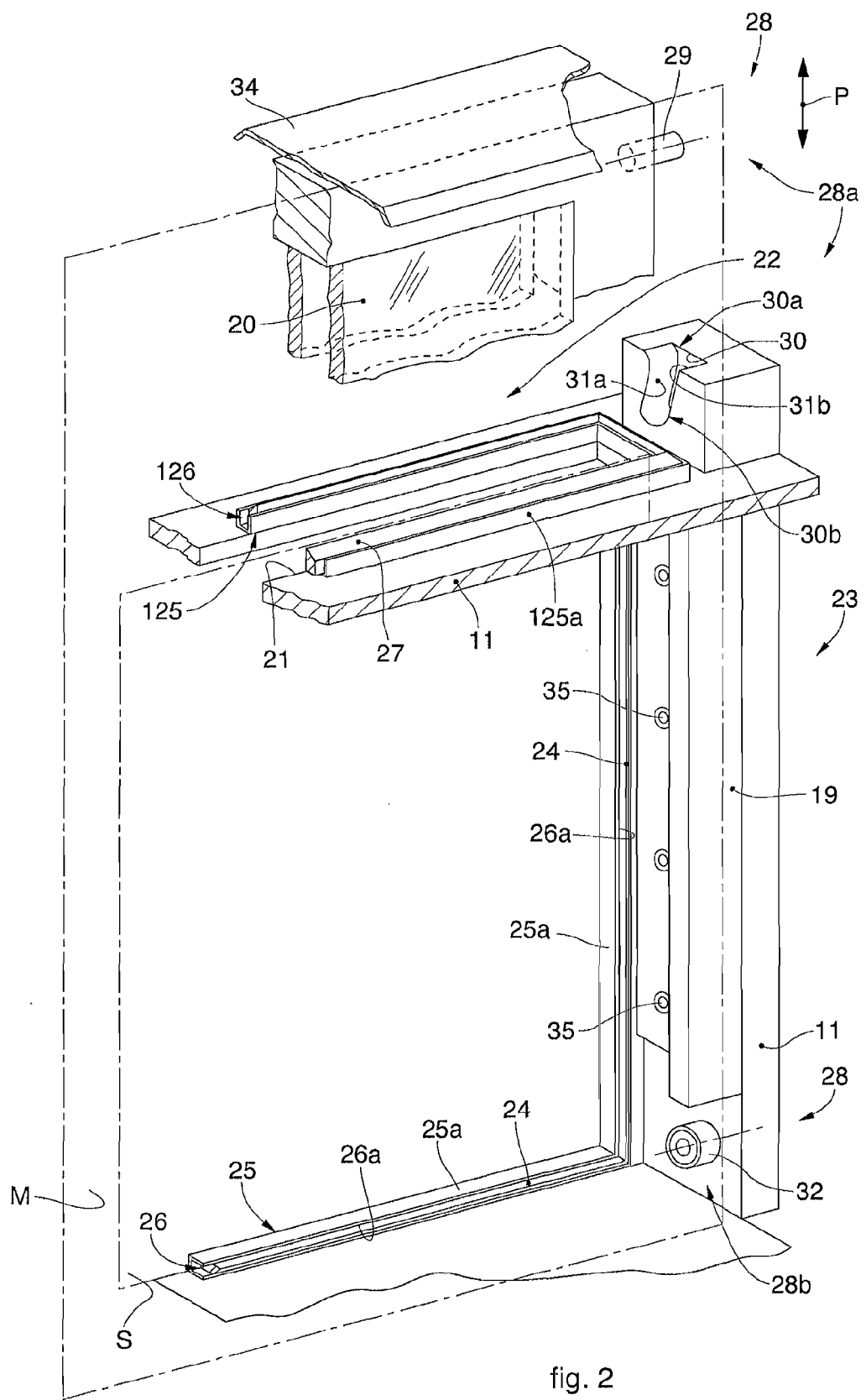
FIG. 2 is a partly sectioned three-dimensional view of the tunnel-type washing machine in FIG. 1.

In some forms of embodiment, shown for example with reference to FIGS. 1 and 2, the passage aperture 21 can be made in the upper part of the containing structure 11, in correspondence with the intermediate zone of the latter, and lies on a plane that is incident, substantially orthogonal, to the movement plane M.

Other forms of embodiment can provide a disposition that is rotated substantially by 90° with respect to what is described here, both of the movement guides 19 and also of the passage aperture 21, that is, if the separation door 20 is mobile horizontally instead of vertically.

The motion of translation of the separation door 20 is provided to make the latter assume at least an open position, in which it is essentially outside the work volume 12, and said closed position, in which the separation door 20 is inside the work volume 12.

In the closed position, the separation door 20 determines a division of the work volume 12 into two processing chambers, in particular a first processing chamber 22 and a second processing chamber 23, contiguous with respect to each other and separated only by the separation door 20.

In FIG. 1, the first 22 and the second processing chamber 23 are shown by way of example in succession in the loading direction F.

The first processing chamber 22 is defined by the portion of the work volume 12 comprised between the entrance door 15 and the separation door 20, while the second processing chamber 23 is defined by the portion of the work volume 12 comprised between the separation door 20 and the exit door 16.

In the forms of embodiment described with reference to FIG. 1, the tunnel-type washing machine 10 comprises only the two processing chambers, first 22 and second 23, cited above.

In other forms of embodiment of the tunnel-type washing machine 10, other processing chambers can be provided, positioned in succession and contiguous in the loading direction F and separated from each other only by a respective separation door 20. Consequently, forms of embodiment described here can provide a tunnel-type washing machine 10 with a plurality of separation doors 20.

FIG. 2 shows a partial section of said intermediate zone of the containing structure 11 of the tunnel-type washing machine 10.

In particular, FIG. 2 shows a part of the intermediate zone, enlarged with respect to FIG. 1. The considerations that will be made for the individual components shown there also apply for other equal or analogous components positioned symmetrically with respect to the longitudinal center line of the containing structure 11 and not shown in FIG. 2 for reasons of descriptive convenience and graphical clarity.

In forms of embodiment described using FIG. 2, the separation door 20 is configured to slide, for example along the movement guides 19, and to translate vertically lying on the movement plane M. In particular, the separation door 20 can slide vertically from the top downward to pass from the open position to the closed position, and vice versa.

As shown by way of example in FIG. 2, the containing structure 11 includes first fluidic sealing means, in particular at least one front packing 24 positioned inside and disposed peripherally on three of the four faces that define the cross section of the containing structure 11. In fact, the front packing 24 is disposed along the sides of the cross section of the containing structure 11 not affected by the passage aperture 21.

In some forms of embodiment, for example in which the cross section of the containing structure 11 is not rectangular, the front packing 24 can be disposed peripherally along the largest part of the cross section, affecting its perimeter except for the portion where the passage aperture 21 is made.

The front packing 24, which acts as a first fluidic sealing mean, can be defined by a single element, such as a strip of polymer material, for example silicon or other elastic and deformable material, substantially U-shaped, or by several rectilinear strips disposed contiguous along the perimeter of the cross section of the containing structure 11, or it can be an inflatable packing, for example made by an air chamber, substantially U-shaped and connected to an inflation device using compressed air, which causes it to expand.

Possibly, means to control the inflation pressure can be provided to monitor the size and to detect possible anomalies or malfunctions, which could cause an insufficient seal and consequent leakage of liquids from the work volume 12, which liquids can also be dangerous or harmful for persons or things present near the tunnel-type washing machine 10.

A first support frame 25 to support the front packing 24 may be provided, which for example can be defined by metal section bars 25a or other analogous or comparable type of section bars, suitably shaped and attached inside the containing structure 11. The metal bars 25a may each delimit a portion 26a of a housing compartment 26 for the front packing 24.

The front packing 24 lies on a sealing plane S parallel to said movement plane M of the separation door 20.

In the specific case shown in the drawings, the sealing plane S is translated with respect to the movement plane M toward the entrance aperture 13, or toward the first processing chamber 22, that is, in the opposite direction with respect to the loading direction F.

It is understood that this description is by way of example only and what is described here can be adapted by the person of skill to a situation where the sealing plane S is translated with respect to the movement plane M in the opposite direction to above, that is, toward the second processing chamber 23.

In some forms of embodiment, the tunnel-type washing machine 10 also includes second fluidic sealing means, in particular an upper packing 27 disposed peripherally around the passage aperture 21. The upper packing 27 advantageously lies on a plane parallel to the one defined by the passage aperture 21. In particular, the upper packing 27 is disposed around the whole perimeter edge that delimits the passage aperture 21.

In the closed position, the separation door 20 is in contact at least with the upper packing 27, thus guaranteeing the fluidic seal of the work volume 12 and hence of the chambers 22, 23 with respect to the outside.

In this case too, as for the front packing 24, for example metal section bars 125a can be provided for the upper packing 27, or other type of analogous or similar section bar, defining a second support frame 125 provided with a housing compartment 126 for the upper packing 27.

In the same way as described above with reference to the front packing 24, the upper packing 27 can also be defined by a single element made with a flexible polymer material, for example a silicon O-ring, or by a plurality of sealing elements positioned around the passage aperture 21, or by an inflatable packing.

The front packing 24 and the upper packing 27 are configured to determine, in cooperation with the separation door 20, the closure with complete fluidic seal of the first processing chamber 22 and the second processing chamber 23 with respect to the outside of the work volume 12, and at the same time to determine the reciprocal sealing of the two processing chambers 22 and 23.

To obtain this result, both the front packing 24 and the upper packing 27 are provided to contact the separation door 20, for example being compressed by the separation door 20 due to the effect of the movement of the latter.

In particular, movement means 28 can be provided, configured to cause a translation of the separation door 20 when it is in the closed position, or in proximity thereof, toward the sealing plane S, so as to pass from said closed position toward another sealing position, different from the closed position both in spatial terms and in functional terms. It is understood that in its passage from the closed position to the sealing position the separation door 20 always remains in contact with the upper packing 27, thus guaranteeing in any case the fluidic seal with respect to the outside during said movement. In fact, the separation door 20 can slide in contact with the upper packing 27 during said passage, as will be described in more detail hereafter in the description.

In the sealing position, the separation door 20 is in contact not only with the upper packing 27 but also with the front packing 24, in particular it is thrust against it, compressing it to determine a desired deformation, and to obtain the sealing of the first processing chamber 22 with respect to the second processing chamber 23. In this way, moreover, the seal is obtained of the first processing chamber 22 with respect to the outside along the portion of cross section of the containing structure 11 affected by the front packing 24.

Figure 3:
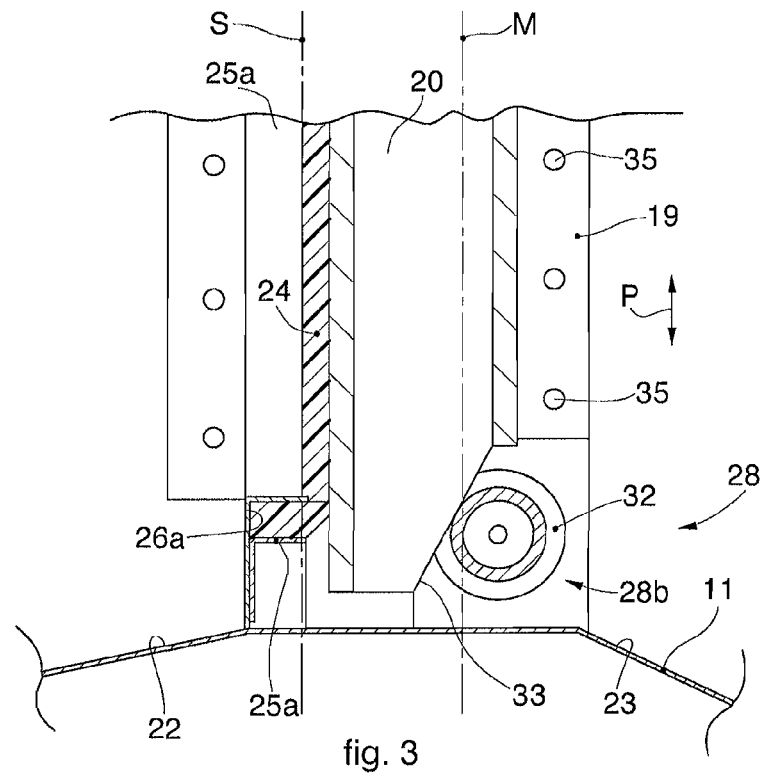
FIG. 3 is a partly sectioned lateral view of the tunnel-type washing machine in FIG. 1.
Figure 4:
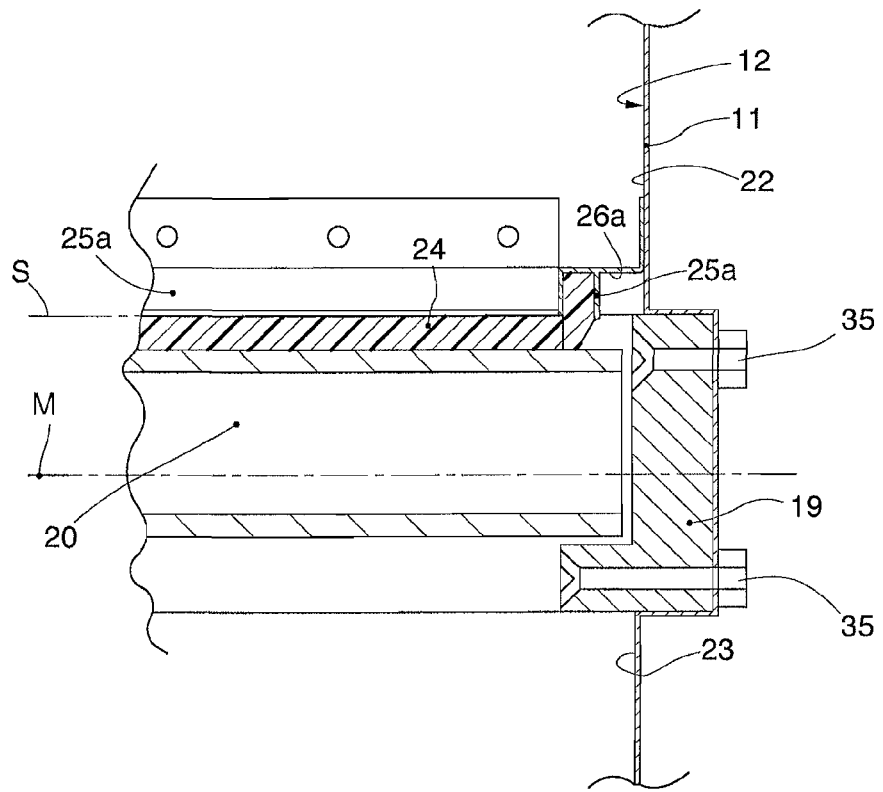
FIG. 4 is a partly sectioned lateral view of the tunnel-type washing machine in FIG. 1.

The sealed condition is shown, using enlargements of details of the tunnel-type washing machine 10, in FIGS. 3 and 4.

In some forms of embodiment, the movement means 28 are thrust means and can include a first thrust unit 28a and a second thrust unit 28b.

In some forms of embodiment, for example described with reference to FIGS. 2 and 3, the movement means 28 can comprise a pair of protruding elements, in this case pins 29 protruding from reciprocally opposite sides of the separation door 20 and mobile solidly therewith.

The pins 29, only one of which is visible in FIG. 2, have an axis substantially parallel to the sealing plane S and perpendicular to the direction of movement P of the separation door 20 defined by the movement guides 19.

Each pin 29 can be provided in the first thrust unit 28a of the movement means 28. The first thrust unit 28a can also include a guide cavity 30, made in the top part of the movement guide 19 and configured to contain the pin 29 when the separation door 20 is in its closed position and to guide it as the separation door 20 passes from the closed position to the other sealing position.

Some simplified forms of embodiment can provide that the guide cavity 30 is made in the containing structure 11, in a portion thereof that is near the passage aperture 21.

The pin 29 is configured to enter into the guide cavity 30 through an opening 30a and slides therein toward a bottom 30b, which it may or may not contact when the separation door 20 is in the sealing position.

For example, the guide cavity 30 can be defined by peripheral walls 31a and 31b, respectively front and rear. At least the rear wall 31b is inclined with respect to the direction of movement P of the separation door 20 from the open position to the closed position.

The inclination of the rear peripheral wall 31b is such that the opening 30a of the guide cavity 30 is positioned nearer the movement plane M with respect to the bottom 30b, which on the contrary is positioned nearer the sealing plane S, and the rear peripheral wall 31b functions as a peripheral guide wall.

During said movement of the separation door 20 downward, the pin 29 enters into contact at least with the rear peripheral wall 31b of the guide cavity 30 on which it slides, and is thrust due to the effect of the inclination of the rear peripheral wall 31b toward the sealing plane S. Since they are solid with the separation door 20, the pair of pins 29 tend to draw the separation door 20 toward the sealing plane S.

In some forms of embodiment, for each lateral part of the separation door 20 where there is a first thrust unit 28a, the movement means 28 can also include a second thrust unit 28b, cooperating with the separation door 20 and with the respective first thrust unit 28a to thrust it and keep it thrust against the front packing 24.

FIG. 3 shows schematically an example of a second thrust unit 28b defined in this case by an overhang 32, which functions as a protruding element and in this specific case is cylindrical in shape, attached to the containing structure 11, and by a sliding wall 33, or peripheral guide wall, which is inclined and for example can be made peripherally in each of the lateral parts of the separation door 20, in its lower end and having the function of peripheral guide wall.

The overhang 32 is only an example of a protruding element, which in some solutions can be fixed, or mobile, for example rotating around its own axis, such as for example a cam or a guide wheel.

In some forms of embodiment, the sliding wall 33 has an inclination such that the separation door 20 has a reduced thickness in its lower end.

When the separation door 20 is moved downward, the sliding wall 33 enters into contact with the overhang 32 which, due to the effect of the inclination of the sliding wall 33, and thanks to the translation movement downward of the separation door 20, thrusts the latter toward the sealing plane S.

Some forms of embodiment, described for example using FIG. 2, provide that the separation door 20 also includes a thrust or compression member 34, configured to enter into contact with the upper packing 27 during the movement of the separation door 20 in the direction of movement P from the open position to the closed position and to contact the upper packing 27, for example to perform a compression of the upper packing 27, deforming it, at the end of the translation toward the closed position.

The compression member 34 can be for example a shaped or profiled sheet having a continuous profile from the separation door 20 toward the outside and along the whole length of the upper packing 27. Furthermore, the compression member 34 can have a bigger plan bulk than that defined by the passage aperture 21 and the upper packing 27 that surrounds it.

In this way, the movement means 28 can guarantee the fluidic seal of the front packing 24, separating and isolating the first processing chamber 22 from the outside and from the second processing chamber 23, while the compression member 34 can guarantee the fluidic seal of the upper packing 27, separating and isolating fluidically both the first processing chamber 22 and the second processing chamber 23 from the outside of the work volume 12.

It is clear that modifications and/or additions of parts may be made to the tunnel-type washing machine 10 as described heretofore, without departing from the field and scope of the present invention.

It is also clear that, although the present invention has been described with reference to some specific examples, a person of skill in the art shall certainly be able to achieve many other equivalent forms of tunnel-type washing machine, having the characteristics as set forth in the claims and hence all coming within the field of protection defined thereby.

The invention claimed is:

1. Tunnel-type machine to wash objects comprising a containing structure which internally delimits a single work volume and which is provided with at least an entrance door to feed the objects in a loading direction, wherein the work volume comprises:
    at least two processing chambers contiguous in the loading direction, a single separation door provided between said two processing chambers, which separation door is configured mobile through a passage aperture of the containing structure, along a movement plane between an open position outside the work volume and a closed position inside the work volume in order to separate the two chambers, said passage aperture lying on a lying plane which is transverse with respect to the movement plane of said separation door,
    said machine comprising:
    at least a front packing between the two processing chambers, positioned inside said containing structure, along at least the greater part of the perimeter of the cross section of the containing structure, and lying on a sealing plane parallel to said movement plane,
    at least an upper packing at the passage aperture, said separation door being configured to contact, in the closed position, both the front packing and the upper packing, movement means comprising a plurality of thrust units operatively coupled to peripheral lateral parts of the separation door and to the containing structure and configured to achieve movement planes of the separation door that are inclined toward the front packing, the plurality of thrust units being configured to move the separation door from the movement plane toward said sealing plane in the loading direction, to determine the passage of said separation door from the closed position to a further sealing position, in which said separation door is in contact not only with said upper packing but also with said first front packing and exerts on the latter a compression thrust in order to obtain the seal; and wherein each thrust unit comprises a protruding element and a peripheral guide wall inclined with respect to said movement plane and said sealing plane, said protruding element and said peripheral guide wall being configured to slide against one another as the separation door moves toward or away from the sealing plane.

2. Tunnel-type machine as in claim 1, wherein said protruding element comprises a pin protruding from said separation door, and wherein said peripheral guide wall is a peripheral wall of a guide cavity made in proximity to the passage aperture and configured to accommodate said pin during the movement of said separation door along said movement plane.

3. Tunnel-type machine as in claim 2, wherein the pin is configured to enter into the guide cavity through an opening and to slide toward a bottom.

4. Tunnel-type machine as in claim 2, wherein the guide cavity is defined by front and rear peripheral walls, at least one rear peripheral wall being inclined with respect to a direction of movement of the separation door from the open position to the closed position.

5. Tunnel-type machine as in claim 4, wherein the inclination of the rear peripheral wall is configured so that the opening of the guide cavity is positioned nearer the movement plane with respect to the bottom positioned nearer the sealing plane and the rear peripheral wall acts as a peripheral guide wall.

6. Tunnel-type machine as in claim 1, wherein said protruding element of said thrust unit comprises an overhang protruding from said containing structure toward the inside of said work volume, and wherein said peripheral guide wall is a lower peripheral wall of said separation door configured to slide on said overhang during the movement of said separation door along said movement plane.

7. Tunnel-type machine as in claim 6, wherein said peripheral guide wall is inclined so that, when the separation door is moved downward, the peripheral guide wall enters into contact with the overhang which, due to the effect of the inclination of the sliding wall and by downward movement of the separation door, the separation door is thrust toward the sealing plane.

8. Tunnel-type machine as in claim 1, wherein said peripheral guide wall has an inclination such that a lower end of the separation door has a reduced thickness.

9. Tunnel-type machine as in claim 1, wherein said upper packing is disposed around the whole perimeter edge which delimits the passage aperture and lies on a plane parallel to the lying plane of said passage aperture, said separation door being configured to cooperate with said upper packing to fluidically separate both said first processing chamber and said second processing chamber from the outside of said work volume.

10. Tunnel-type machine as in claim 1, wherein said separation door comprises a thrust or compression member sized to be greater than a size of said passage aperture and a size of the upper packing, and wherein the thrust or compression member is configured to contact said upper packing when said separation door is in the closed position.

11. Tunnel-type machine as in claim 1, wherein the containing structure has an entrance aperture and the loading direction is transverse to the lying plane of the entrance aperture.

12. Tunnel-type machine as in claim 11, wherein the containing structure has an exit aperture, wherein the entrance aperture and the exit aperture are respectively provided with perimeter edges with which packings cooperate able to be thrust or compressed, respectively by the entrance door and by an exit door provided to close the exit aperture, in order to obtain a hermetically sealed closure of the work volume.

13. Tunnel-type machine as in claim 1, further comprising at least two linear movement guides made laterally with respect to the cross section of the containing structure and configured to guide a translation of the separation door in a direction of movement transverse with respect to the loading direction.

14. Tunnel-type machine as in claim 1, further comprising a first support frame of the front packing.

15. Tunnel-type machine as in claim 14, wherein said first support frame is defined by metal section bars attached inside the containing structure and shaped to each delimit a portion of a housing compartment for the front packing.

16. Tunnel-type machine as in claim 1, further comprising a second support frame of the upper packing.

17. Tunnel-type machine as in claim 16, wherein said second support frame is defined by metal section bars which define a housing compartment for the upper packing.

* * * * *